(12) United States Patent
Kim et al.

(10) Patent No.: US 8,399,221 B2
(45) Date of Patent: Mar. 19, 2013

(54) METHODS FOR DETECTION AND QUANTITATION OF SMALL RNAS

(75) Inventors: Daniel Y. Kim, Centreville, VA (US); Yexun Wang, Ellicott City, MD (US)

(73) Assignee: SABiosciences Corporation, Frederick, MD (US)

( * ) Notice: Subject to any disclaimer, the term of this patent is extended or adjusted under 35 U.S.C. 154(b) by 0 days.

(21) Appl. No.: 12/291,010

(22) Filed: Nov. 4, 2008

(65) Prior Publication Data

US 2010/0112644 A1    May 6, 2010

(51) Int. Cl.
*C12P 19/34* (2006.01)
*C07H 21/02* (2006.01)
*C07H 21/04* (2006.01)

(52) U.S. Cl. ............... 435/91.1; 435/91.2; 536/23.1; 536/24.5

(58) Field of Classification Search .................. None
See application file for complete search history.

(56) References Cited

U.S. PATENT DOCUMENTS

| | | | |
|---|---|---|---|
| 5,256,555 A | 10/1993 | Milburn et al. | |
| 2006/0094025 A1* | 5/2006 | Getts et al. | 435/6 |
| 2008/0003574 A1* | 1/2008 | Michalik et al. | 435/6 |

OTHER PUBLICATIONS

Sioud et al., Profiling microRNA expression using sensitive cDNA probes and filter arrays, 2004, BioTechniques, vol. 37, pp. 574-580.*
BD PowerScript™ Reverse Transcriptase, BD Biosciences Clontech, Jan. 2004, Clontechniques Product Overview, p. 5.*
Superscript™ II Reverse Transcriptase, Invitrogen Life Technologies, 2003, Catalog information, 4 pages are enclosed.*
SYBR® Green PCR Master Mix and RT-PCR protocol, Applied Biosystems, printed in the USA, Apr. 2002.*
Markou et al., Prognostic value of mature microRNA-21 and microRNA-205 overexpression in non-small cell lung cancer by quantitative real-time RT-PCR, 2008, Clinical Chemistry, vol. 54, pp. 1696-1704.*
Deprez et al., Sensitivity and accuracy of quantitative real-time polymerase chain reaction using SYBR green I depends on cDNA synthesis conditions, 2002, Analytical Biochemistry, vol. 307, pp. 63-69.*
Seto et al., The coming of age for Piwi proteins, 2007, Molecular Cell, vol. 26, pp. 603-609.*
Meenakshisundaram et al., Existence of snoRNA, microRNA, piRNA characteristics in a novel non-coding RNA: x-ncRNA and its biological implication in *Homo sapiens*, 2009, Journal of Bioinformatics and Sequence Analysis, vol. 1, pp. 031-040.*
Ambion (2007) mirVana miRNA Labeling Kit, Cat # Am1562, Ambion, Inc.
Bukhman et al. (1997) "Affinities and Selectivity's of Divalent Cation Binding Sites Within an RNA Tertiary Structure," *J. Mol. Biol.* 273:1020-1031.
Cao et al. (Oct. 1996) "Identification of the Coding Region for a Second Poly(A) Polymerase in *Escherichia coli*," *Proc. Nat. Acad. Sci. USA* 93:11580-11585.
Draper et al. (2004) "A Guide to Ions and RNA Structure," *RNA* 10:335-343.
Kumar et al. (Feb. 1, 2008) "RNA Interference: A Multifaceted Innate Antiviral Defense," *Retrovirology* 5:17.
Lee et al. (Jan. 24, 2008) "Discriminating Single-Base Difference miRNA Expressions Using Microarray Probe Design Guru (ProDeG)," *Nuc. Acids Res.* 36(5):e27.
Lee et al. (Dec. 3, 1993) "The *C. elegans* Heterochronic Gene *Lin-4* Encodes Small RNAs with Antisense Complementarity to *Lin-14*," *Cell* 75:843-854.
Newton et al. (1989) "Analysis of any Point Mutation in DNA. The Amplification Refractory Mutation System (ARMS)," *Nuc. Acids Res.* 17(7):2503-2516.
Qiagen (Apr. 2007) "MiScript System Handbook," QIAGEN Publication.
QIAGEN (Jan. 2008) "Quantitect SYBR Green PCR Handbook," QIAGEN Publication.
Ro et al. (Oct. 30, 2006) "A PCR-Based Method for Detection and Quantification of Small RNA's," *Biochem. Biophys. Res. Commun.* 351:756-763.
SA Biosciences (2008) "MicroRNA PCR Arrays," Available on the Internet from the SABiosciences Website.
Shi et al. (2005) "Facile Means for Quantifying MicroRNA Expression by Real-Time PCR," *BioTechniques* 39(4):519-524.
SuperArray (Feb. 29, 2008) "User Manual: RT2 miRNA qPCR Assays," Part #1032A.
Tinsley et al. (2006) "Pyrrolo-C as a Fluorescent Probe for Monitoring RNA Secondary Structure Formation," *RNA* 12:522-529.
Yehudai-Resheff et al. (2000) "Characterization of the *E.coli* Poly(A) Polymerase Nucleotide Specificity, RNA-Binding Affinities and RNA Structure Dependence," *Nuc. Acids Res.* 28(5):1139-1144.

* cited by examiner

*Primary Examiner* — Dana Shin
(74) *Attorney, Agent, or Firm* — SEED IP Law Group PLLC

(57) ABSTRACT

Improved methods that increase the specificity and sensitivity of detection of small RNAs, including miRNAs, using oligonucleotide primers and nucleic acid amplification, are provided. Reaction conditions that result in preferential decrease in cDNA synthesis of RNAs other than the small RNA molecules targeted for detection during miRNA tailing and reverse transcription reactions are described. Using these reaction conditions greater sensitivity and specificity of amplification of small RNAs including miRNAs is achieved.

8 Claims, 15 Drawing Sheets
(5 of 15 Drawing Sheet(s) Filed in Color)

SEQUENCE LISTING

<160> NUMBER OF SEQ ID NOS: 7

<210> SEQ ID NO 1
<211> LENGTH: 52
<212> TYPE: DNA
<213> ORGANISM: Artificial Sequence
<220> FEATURE:
<223> OTHER INFORMATION: Synthetic construct: reverse transcription
   primer for poly(A) tailed RNA
<220> FEATURE:
<221> NAME/KEY: misc_feature
<222> LOCATION: (51)..(51)
<223> OTHER INFORMATION: At position 51, V is G or A or C.
<220> FEATURE:
<221> NAME/KEY: misc_feature
<222> LOCATION: (52)..(52)
<223> OTHER INFORMATION: At position 52, N is G or A or C or T.

<400> SEQUENCE: 1
gtgcagggtc cgaggttcac tataggtttt tttttttttt tttttttttt vn      52

<210> SEQ ID NO 2
<211> LENGTH: 23
<212> TYPE: DNA
<213> ORGANISM: Artificial Sequence
<220> FEATURE:
<223> OTHER INFORMATION: Synthetic construct: forward PCR primer for
   hsa-miR-346

<400> SEQUENCE: 2
tgtctgcccg catgcctgcc tct                                      23

<210> SEQ ID NO 3
<211> LENGTH: 23
<212> TYPE: DNA
<213> ORGANISM: Artificial Sequence
<220> FEATURE:
<223> OTHER INFORMATION: Synthetic construct: forward PCR primer for
   hsa-miR-10a

<400> SEQUENCE: 3
taccctgtag atctgaattt gtg                                      23

<210> SEQ ID NO 4
<211> LENGTH: 22
<212> TYPE: DNA
<213> ORGANISM: Artificial Sequence
<220> FEATURE:
<223> OTHER INFORMATION: Synthetic construct: forward PCR primer for
   hsa-miR-504

-continued

```
<400> SEQUENCE: 4
accctggtct gcactctatc aa                                                    22

<210> SEQ ID NO 5
<211> LENGTH: 21
<212> TYPE: DNA
<213> ORGANISM: Artificial Sequence
<220> FEATURE:
<223> OTHER INFORMATION: Synthetic construct:  forward PCR primer for
      hsa-miR-555

<400> SEQUENCE: 5
ggtaagctga acctctgata a                                                     21

<210> SEQ ID NO 6
<211> LENGTH: 25
<212> TYPE: DNA
<213> ORGANISM: Artificial Sequence
<220> FEATURE:
<223> OTHER INFORMATION: Synthetic construct:  forward PCR primer for
      hsa-miR-658

<400> SEQUENCE: 6
ggcggaggga agtaggtccg ttggt                                                 25

<210> SEQ ID NO 7
<211> LENGTH: 16
<212> TYPE: DNA
<213> ORGANISM: Artificial Sequence
<220> FEATURE:
<223> OTHER INFORMATION: Synthetic construct:  universal reverse PCR
      primer for cDNAs  generated using SEQ ID NO:1 pirmer.

<400> SEQUENCE: 7
gtgcagggtc cgaggt                                                           16
```

METHODS FOR DETECTION AND QUANTITATION OF SMALL RNAS

CROSS-REFERENCE TO RELATED APPLICATIONS

Not applicable.

STATEMENT REGARDING FEDERALLY SPONSORED RESEARCH OR DEVELOPMENT

Not Applicable

REFERENCE TO SEQUENCE LISTING

The Sequence Listing is incorporated by reference herein.

BACKGROUND OF THE INVENTION

The methods disclosed herein relate to detecting and quantifying nucleic acids, especially small RNAs, including miRNAs and genes coding for small RNAs including but not limited to miRNAs. In the disclosure various reactions may be described in respect to miRNA, but it is understood by those skilled in the art that such reactions or reaction conditions would apply similarly to other small RNAs, of which miRNAs are an important subclass. More specifically, the present methods relate to novel reaction conditions under which a homopolymeric tail is added to the 3' end of a small RNA using poly-adenosine (poly(A)) polymerase (polyadenylation) and subsequently rendered into cDNA by reverse transcriptase under conditions that permit greater discrimination of a target miRNA from non-miRNA contained in the same sample. These novel reaction conditions lead to greater specificity of addition of nucleotides by both polymerases and greater specificity of detection of the small RNA being assayed. These reaction conditions allow for convenient use of both poly(A) polymerase and reverse transcriptase under substantially the same ionic and buffer conditions, thereby avoiding undesired dilution of the sample or purification of products (with potential loss of desired materials) between the poly(A) polymerase reaction and the synthesis of a cDNA copy catalyzed by reverse transcriptase. The ability to forego all purification or substantial dilution of sample between these two reactions as well as subsequent reactions that measure miRNA amounts greatly increases the ease of the assay, as well as its reproducibility, accuracy and sensitivity.

MicroRNAs (miRNA) are single-stranded RNA molecules of about 18 to 28, often about 22, nucleotides in length, which regulate gene expression. Other small RNAs, including piRNAs, snoRNAs, and small guide or sgRNAs, play essential biological roles, and their detection and quantitation are desired. Still other small RNAs may be discovered that play important biological roles as well. Herein a small RNA is defined as an RNA shorter than about 100 nucleotides in length. All miRNAs, piRNAs, sgRNAs, snoRNAs and snRNAs, as well as other RNAs having fewer than 100 nucleotides are "small RNAs". These RNAs are encoded by genes that are transcribed from DNA, but the transcription products are not translated into protein (non-coding RNA). They are, in the case of miRNAs, processed from primary transcripts known as pri-miRNA to short stem-loop structures called pre-miRNA and finally to functional miRNA. Mature miRNA molecules generally are partially complementary to one or more messenger RNA (mRNA) molecules, and their principal regulatory function is to down-regulate gene expression by translation repression. They were first described in 1993 by Lee and colleagues and are today recognized as important regulatory molecules in eukaryotic cells. MicroRNAs have been shown to play key roles in development, apoptosis, and cancer. They have also been shown to be coded for by certain viruses.

Specific, sensitive and quantitative detection and assay of individual small RNAs and detection of miRNAs play an especially important role in biomedical and biological research and promise to be of diagnostic and prognostic value in medical practice as well.

Notwithstanding their importance as regulatory molecules, small RNAs represent a small fraction of the RNA species in a eukaryotic cell. Because they are short, in the case of miRNAs, about 18-28 nucleotides in length, or 18-50, or 18-100, and share homology or partial homology, with the genes they regulate, detection of specific miRNAs and especially accurate quantitation of miRNAs present experimental challenges. Improvements to methods for the specific detection and quantitation of miRNAs will accelerate basic research. Improved assays of miRNAs can prove of diagnostic or prognostic value in medicine.

One of the most widely used and effective ways to detect and quantify RNAs is to produce a complementary DNA (cDNA) transcript of specific RNA, and then to amplify that DNA using the polymerase chain reaction (PCR) under conditions where the accumulation of the amplified product is monitored during the amplification, usually by means of fluorescent molecules added to the PCR. This method is widely known as Real-Time Quantitative RT-PCR (RT-qPCR). Improved methods to assay specific miRNAs by RT-qPCR are desired.

When assaying for species as low in abundance as miRNA, the specificity of detection and accurate quantitation are usually higher priorities than absolute analytical sensitivity. Accordingly, modifications to standard processes that increase specificity and accuracy of quantitation, even if they result in minimal or modest losses of absolute analytical sensitivity, are likely to be preferred.

In light of the vast abundance of RNAs other than the specific small RNA being assayed, or especially in the case of assaying for a specific miRNA, non-specific amplification of other sequences can compromise the sensitivity, specificity, and precision of an RT-qPCR assay for a small RNA, especially an miRNA.

One approach to the specific amplification of miRNAs, but also applicable to other small RNAs, is that used by Ro et. al. (Biochem Biophys Res Commun (2006) 351 (3) 756-763) which involves addition to the 3' prime end of the miRNA to be amplified (the target miRNA) a poly(A) tail of greater than about 20 base pairs. This can be done using poly(A) polymerase and ATP; this lengthens the miRNA molecule in order to facilitate subsequent cDNA synthesis and detection. An oligonucleotide, with the 5' sequence region matching a universal qPCR primer sequence and the 3' sequence region being approximately 20 d(T) bases and complementary to the poly(A) tail, is hybridized to the 3' end of the target miRNA to provide a template which can be used by a reverse transcriptase to produce a cDNA molecule capable of being amplified by PCR. This cDNA contains a region complementary to a specific miRNA, a central region of approximately 20 T's (on one strand and the same number of A's on the other) and a third region that contains an arbitrary sequence that can serve well as a site for specific priming by a PCR primer, i.e., a universal primer. Note, that cDNAs made from different miRNAs, will have all have a common universal primer sequence. However, this reaction is not absolutely specific and other RNAs present in the sample and such other RNAs having been present in vast abundance relative to the targeted miRNA in the cells, from which the miRNA is prepared, in spite of earlier purification steps taken to eliminate them, may have poly(A) tails added to them. Some of these non-miRNAs may also serve as template for reverse transcriptase and receive a universal primer sequence. Reduction in non-specific tailing of RNAs and generation of RNAs other than miRNAs that contain universal primer sequence is desired. All of the advantages described above pertaining to miRNAs also apply to other small RNAs.

Purified poly-adenosine polymerase has been commercially available for years to artificially produce poly(A) tails on RNA molecules in vitro. Recently this enzymatic activity has been utilized as the first step in an miRNA cDNA generation system to increase the length of the miRNA for increased PCR performance and to provide a uniform primer binding site to initiate cDNA synthesis.

Purified reverse transcriptases have been used to produce DNA copies of RNAs in vitro following well accepted reaction conditions and protocols. This reaction has become a standard process used in thousands of research laboratories. Several manufacturers of research products have marketed kits containing premixed buffers for customer use. Like most enzymes that catalyze the polymerization of nucleotide triphosphates into DNA or RNA using a template nucleic acid as a template, reverse transcriptases have standard reaction conditions in which the concentration of magnesium ions is maintained between about 2 millimolar and 5 millimolar. Biochemists experienced in the optimization of reverse transcriptase reaction in vitro are especially careful to optimize the concentration of magnesium ions within this overall range, about 2 millimolar to about 5 millimolar. The Applicants are unaware of any published reports of reaction conditions for reverse transcription in vitro carried out with a magnesium concentration above 10 mM.

The concentration of cations, particularly divalent cations such as magnesium and manganese are known to affect the secondary structure of nucleic acids, particularly single stranded nucleic acids such as most RNAs found in cells, including human cells (Bukhman and Draper, J. Mol. Biol. (1997) 273, 1020-1031) Nearly all RNAs that are abundant in cells, especially, but not only ribosomal RNAs, have considerable secondary structure that can be affected by the ionic environment, especially the concentration of cations such as magnesium and manganese. While methods are known that result in the preferential purification of small RNAs, miRNA purified using these methods can be heavily contaminated with larger RNAs, with other small RNAs, and degradation fragments of large RNAs such as ribosomal RNAs. In any sample of RNA, even one enriched for shorter RNAs, any particular miRNA will be a minor constituent in the sample. Thus, there is a need in the art for improved methods which allow selective amplification of one or more target small RNA molecules in a sample.

SUMMARY OF THE INVENTION

The invention comprises a new and improved method for synthesis of a cDNA that contains the sequence of an miRNA or other small RNA that can be amplified using standard nucleic acid amplification methods such as the Polymerase Chain Reaction is disclosed. The method disclosed herein provides higher specificity of cDNA synthesis from small RNAs, while simultaneously permitting experimenters to carry out the two key enzymatic reactions necessary for this synthesis under substantially the same reaction conditions, conditions that include the presence of divalent cations at concentrations from 10 millimolar and 80 millimolar. When these reactions conditions are used as part of an assay for a small RNA, especially for an miRNA, greater specificity and sensitivity results.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-4B 4 show the benefit of performing the cDNA synthesis of small RNA targets under conditions of high Mg (FIG. 4B), which extends to the use of human total RNA samples as a target source material as compared under conditions of low Mg (FIG. 4A). This is indicated by the overall increase in Ct values obtained from qPCRs across 376 assays in a human miRNA assay library in the dissociation curves. Ct values greater than 35 are considered to be below the level of quantitative detection by this qPCR.

DETAILED DESCRIPTION OF THE INVENTION

Figure 1A:
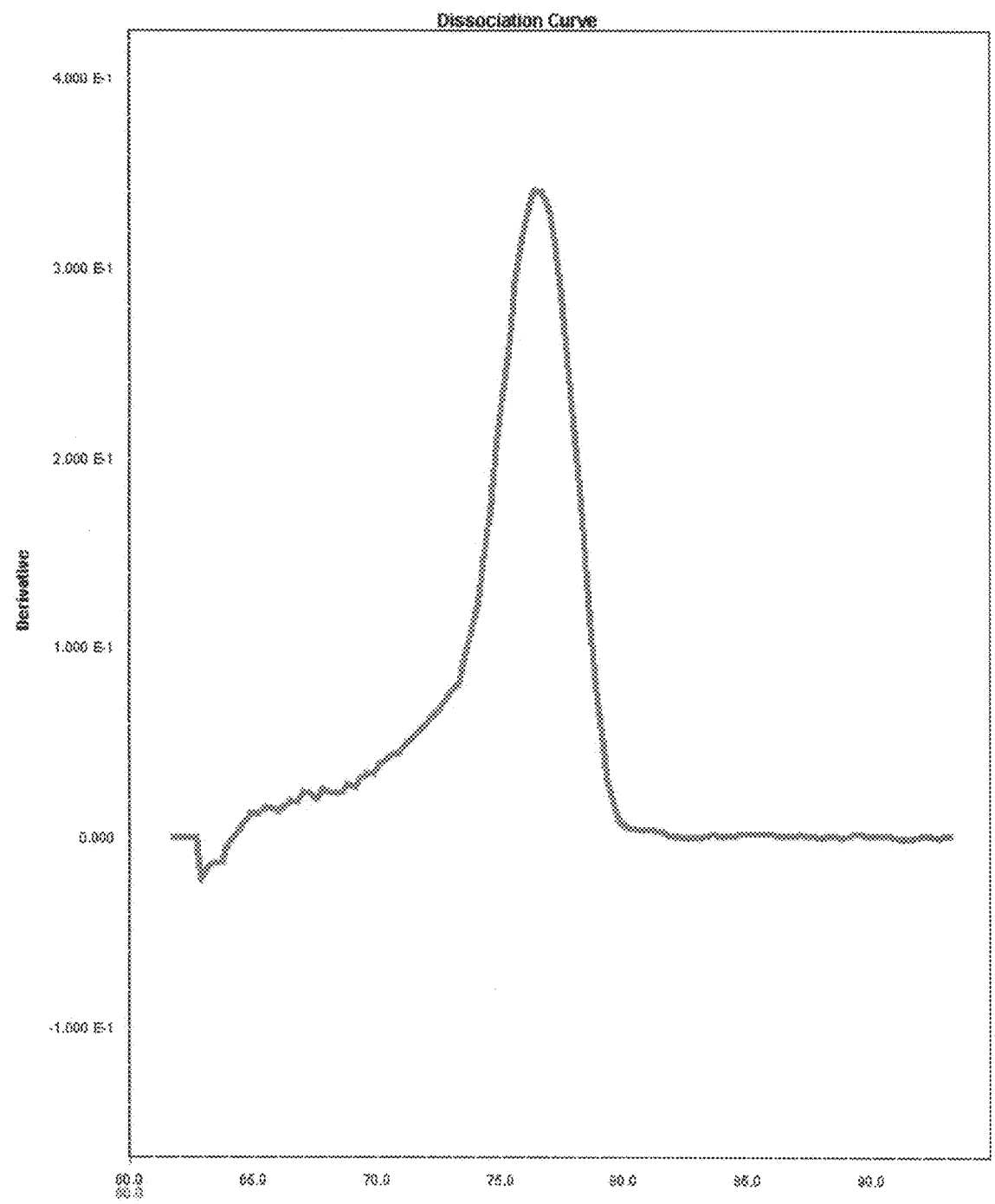
FIG. 1A is an exemplary first derivative of the thermal dissociation curve for a miRNA specific qPCR reaction in which there is good specificity of the resulting products, as indicated by a single major peak.

In the present context, miRNA is referred to because it is an archetype of the small RNAs for which the present methods are especially well suited; however, all the advantages pertaining to the present methods for detection of miRNA are similarly applicable to detection of all short RNAs. Notwithstanding the well accepted range of magnesium ion concentration appropriate for poly(A) tailing and reverse transcription, alternative reaction conditions, in which magnesium ions are included at significantly higher concentration than 5 millimolar are disclosed herein, and such conditions have been found to be compatible with efficient catalysis by reverse transcriptase. Surprisingly, these conditions increase the specificity of addition of poly(A) tails to a desired target miRNAs while minimizing addition of poly(A) tails to small RNA molecules longer than miRNAs.

MicroRNAs (miRNA) are single-stranded RNA molecules of about 15 to about 50 nucleotides, or up to 75 or up to 100 nucleotides, especially about 18 to 28 nucleotides in length, which regulate gene expression. Other small RNAs, include piRNAs and snoRNAs. piRNAs are Piwi-interacting RNAs; they are expressed in mammalian testes and somatic cells and they form RNA-protein complexes with Piwi proteins. The piRNAs function in gene silencing of retrotransposons and other genetic elements in germ line cells. Typically, piRNAs are about 26-31 nucleotides long. Generally the snoRNAs are in the range of about 70 to about 185 nucleotides in length. However, the specificity for amplification is increased with small RNA molecules up to about 100 nucleotides in length.

Insofar as miRNAs and other small RNAs are short in length, on the order of a typical primer used for extension of a template, little flexibility is available in terms of sequence selection for a PCR primer. The shorter the RNA, the less flexibility of primer selection is generally available. This contrasts with larger RNAs such as mRNAs where multiple primers can be considered and tested, and those that exhibit unacceptably low priming efficiency or specificity may be avoided. In the case of an miRNA and other small RNA molecules, few primer options are available, and all (or most) of them share considerable sequence homology or overlap with one another. If a priming sequence exhibits unacceptable priming specificity (FIG. 1), the experimenter must find approaches other than alternative priming sites to increase assay specificity.

In most applications in which one desires to add a poly(A) region to the 3' end of a collection of RNAs, optimal performance entails having the enzyme add poly(A) to all of the RNAs in the collection and to do so with substantially the same efficiency for each RNA in the sample. In the situation in which one wished to detect miRNAs or other small RNAs that are represented in the mixture at low levels, conditions that preferentially add poly(A) to miRNAs or other small RNAs are desirable, even if these conditions lower the efficiency of tailing for the desired miRNA or small RNA.

It was found that if the concentration of magnesium ions present in both the poly(A) tailing and reverse transcription reaction mixture is about 50 to 70 mM, a concentration far higher than has been previously used in vitro for both enzymes, the desired tailing reaction proceeds efficiently and the specificity of addition of poly(A) tails to the desired miRNAs is enhanced (FIG. 2). At the same time, non-target RNAs, which are also potential substrates for the enzymes, take on characteristics under high magnesium conditions that reduce the efficiency of tailing their 3' end. Because the specificity of addition of poly(A) tails is of high importance, the specificity and sensitivity of detection and the precision of quantitation of specific miRNAs or other small RNA is increased. The optimal concentration for enhancing the specificity of poly(A) tailing with poly(A) polymerase may vary according to the miRNA or other small RNA an investigator desires to detect and quantify, but absolute optimization may not be required. The present inventors have concluded that a concentration of magnesium ions in the range of 50 to 70 mM is suitable for all miRNAs or other small RNAs, providing significantly increased specificity and sensitivity as compared to reaction conditions in which a magnesium concentration is in the range of 2 mM to 5 mM, the range heretofore typically used for in vitro reverse transcription. Furthermore, it has been observed that the generation of cDNA through the use of reverse transcriptase can also be carried out at a magnesium ion concentration in the range of about 50 mM to 70 mM, a concentration that has never been reported as suitable for polymerization by reverse transcriptase. Insofar as reverse transcription to yield cDNA immediately follows tailing by poly(A) polymerase and it is not advantageous to dilute the reaction, the ability to carry out reverse transcription at a magnesium ion concentration in the range of 50 to 70 mM provides significant benefit in terms of product yield, experimental efficiency and convenience (FIG. 3).

While divalent manganese cations have the beneficial effect on the reverse transcriptase step, the use of manganese is not preferred because of the inhibitory effects on certain polymerases (especially Taq polymerase) used in the amplification reaction. Thus, purification away from the manganese is required if the Taq (or equivalent) polymerase is to be used.

Without wishing to be bound by theory, it is believed that the mechanism for the observed effect of magnesium at a concentration from about 50 mM to about 70 mM, is the stabilization of secondary structure and internal base pairing in RNAs which are longer than miRNAs, which are present in the preparation despite efforts to eliminate them by prior purification. This increased stability of secondary structure and intramolecular base pairing is believed to reduce the availability of the 3' RNA terminal to occupy the catalytic site of the poly(A) polymerase and to reduce the ability of the reverse transcriptase primer oligonucleotide to hybridize to RNAs other than the miRNA or other small RNA being targeted, but which share partial homology to the targeted miRNA or other small RNA. Being short, in the range of 18 to 28 bases in length, miRNAs have little ability to form secondary structure even with the stabilizing effects of elevated magnesium concentration. Other small RNAs are expected to have similarly reduced ability to form secondary structure. No significant reduction in tailing of miRNAs has been observed using poly(A) polymerase at magnesium concentrations in the range of 60 mM to 70 mM as compared to tailing at magnesium concentrations in the commonly used range of 2 mM to 5 mM.

While most users of reverse transcriptase use a reverse transcriptase encoded by Mouse Moloney Leukemia Virus or a genetically engineered mutated form of this enzyme, other reverse transcriptases may be used and the improved reaction conditions comprising elevated magnesium concentration confer the same or similar advantages if these other reverse transcriptases are used.

By inhibiting hybridization by the DNA oligonucleotide primer, the elevated magnesium reduces reverse transcription of these longer, non-targeted RNAs.

Increasing the concentration of magnesium ions to preferentially stabilize the secondary structure of non-mi-RNAs has been used because magnesium is known to be compatible with efficient catalysis by reverse transcriptases. Other cations, especially other divalent cations, such as manganese, may provide similar improved specificity of tailing without unacceptably reducing the catalytic efficiency of reverse transcriptase.

Figure 1B:
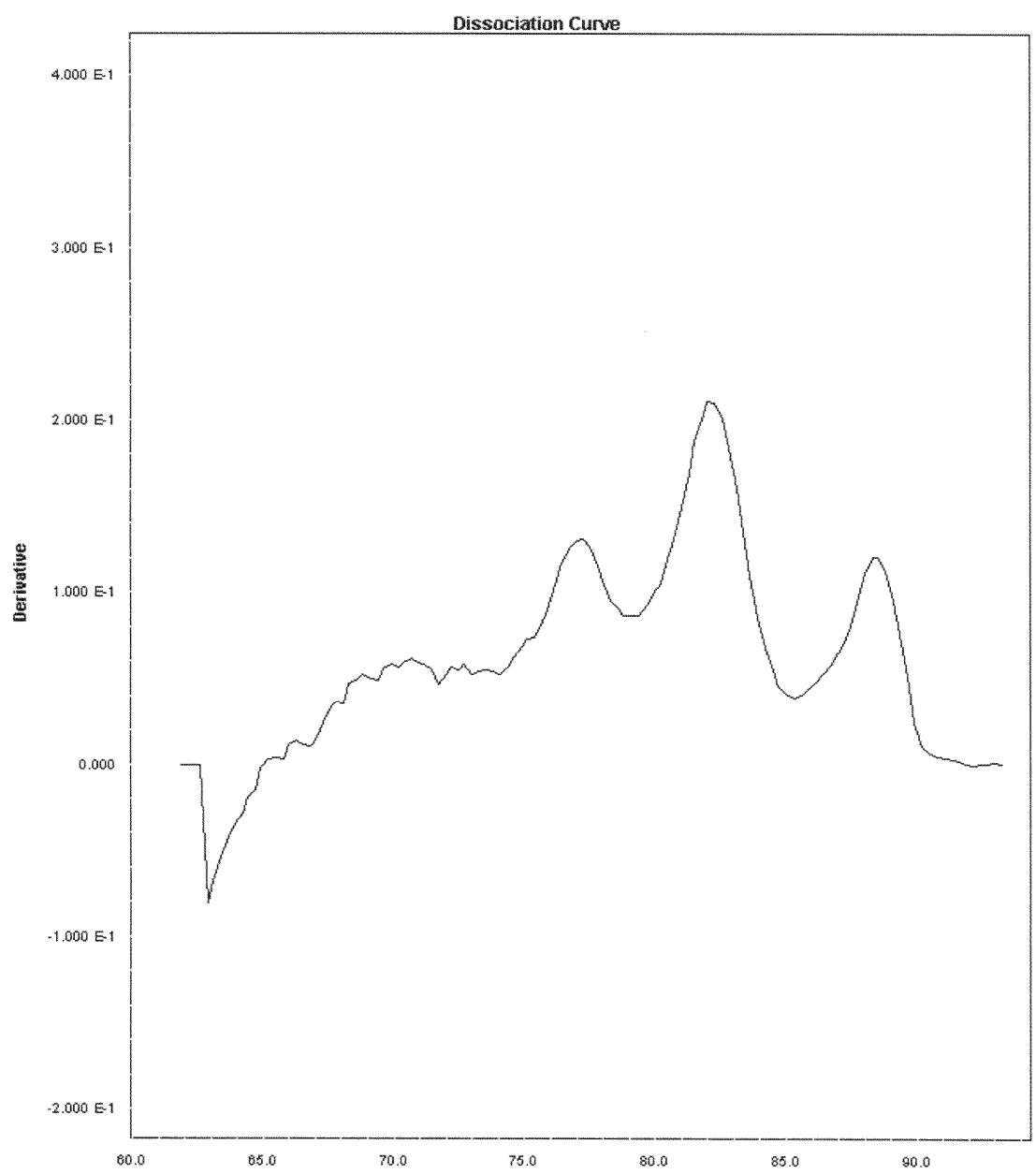
FIG. 1B is an exemplary "Bad Assay", reflected in a thermal dissociation curve whose shape results from an unacceptable level of non-specific amplification as indicated by more than one major peak.

A key measure of the efficiency and specificity of the tailing reaction is the frequency at which non-specific amplification becomes so high as to render results unreliable. In Table 1 multiple reactions (468 different human miRNA qPCR assays) were carried out using a range of magnesium chloride concentrations in the tailing reaction and qPCR. Two different input RNA levels were also used. Reactions conducted using 50 mM or 70 mM $MgCl_2$ consistently showed a lower percentage of reactions exhibiting unacceptable high levels of non-specific amplification. "Bad Assays" as a descriptor in Table 1 are ones in which the thermal dissociation curve of the amplification products indicated non-specific amplification as evidenced by more than one peak. Four different cell lines were used as a source of miRNA for all 468 assay and a "Bad" result from even a single cell line was tallied as a "Bad" result in the table. An example of the melting curve of an assay that is not a "Bad Assay" is shown in FIG. 1A and an example of a "Bad Assay" is shown in FIG. 1B.

In addition, the results in Table 1 demonstrate that the $MgCl_2$ effect occurs only during the cDNA synthesis step and not the qPCR steps. This is evident from the fact that the 3 mM "plus" column results, where the tailing and RT were performed at 3 mM but the qPCR performed at the level equivalent to 70 mM, match the standard 3 mM results and not the 70 mM results.

TABLE 1

Tailing/RT qPCR results for a human miRNA assay library tested on 4 human cell lines under different conditions of MgCl2 and RNA template input.

| [MgCl$_2$] (RNA input) | 3 mM (50 ng RNA) | 50 mM (50 ng RNA) | 70 mM (50 ng RNA) | 3 mM (100 ng RNA) | 3 mM "plus" (100 ng RNA) | 70 mM (100 ng RNA) |
|---|---|---|---|---|---|---|
| "Bad" Results out of 468 Assays | 271 | 213 | 170 | 241 | 244 | 152 |

All references cited herein are hereby incorporated by reference to the extent they are not inconsistent with the present disclosure, and for example, a reference that is partially inconsistent is incorporated by reference except for the partially inconsistent portion of the reference. Those references reflect the state of the art and the level of skill in the relevant art. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

Although the description herein contains certain specific information, these should not be construed as limiting the scope of the invention but as merely providing illustrations of some of the presently preferred embodiments of the invention. For example, thus the scope of the invention should be determined by the appended claims and their equivalents, rather than by the examples given.

When a compound or concentration in a method is claimed, it should be understood that compounds and concentrations known in the art including those disclosed in the references disclosed herein are not intended to be included. When a Markush group or other grouping is used herein, all individual members of the group and all combinations and subcombinations possible of the group or range are intended to be individually included in the disclosure.

Every formulation or combination of components described or exemplified can be used to practice the invention, unless otherwise stated. Specific names of compounds and enzymes are intended to be exemplary, as it is known that one of ordinary skill in the art can name the same compounds and enzymes differently. When a compound or enzyme is described herein such that a particular isomer, enantiomer or isoform of the compound or enzyme is not specified, for example, in a formula or in a chemical name, that description is intended to include each isomer, enantiomer or isoform of the compound or enzyme described individual or in any combination.

One of ordinary skill in the art will appreciate that methods, enzymes or starting materials, other than those specifically exemplified can be employed in the practice of the invention without resort to undue experimentation. All art-known functional equivalents, of any such methods, device elements, starting materials, synthetic methods, and enzymes are intended to be included in this invention. Whenever a range is given in the specification, for example, a concentration range, a temperature range, a time range, or a composition range, all intermediate ranges and subranges, as well as all individual values included in the ranges recited are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art.

The invention may be further understood by the following non-limiting examples.

EXAMPLES

Example 1

Cultured mammalian cells (MCF7, 293H, SKBR3 or Jurkat) were harvested into a pellet containing up to 5×10$^6$ cells per tube. One ml of Trizol® (Invitrogen, Carlsbad, Calif.) was added, mixed and allowed to incubate at room temperature (RT) for 5 minutes. 200 µl of chloroform was added, mixed and centrifuged for 5 minutes at 12,000×g at 4° C. 400 µl of the upper aqueous phase was transferred to a new tube and mixed with 215 µl ethanol. This mixture was applied to a NucleoSpin® RNA II spin column (Macherey-Nagel, Düren, Germany) and centrifuged for 30 seconds at 11,000×g at RT. The eluate from the column, which contains small RNA, was mixed with 750 µl ethanol and applied to a second spin column as described above. Under the condition of greater ethanol concentration, the small RNA was retained on the column. The column was washed by adding 200 µl wash buffer (1 part RA3 Buffer (Macherey-Nagel, Düren, Germany) plus 4 parts 100% ethanol) and centrifuging for 30 seconds at 11,000×g at RT. This was followed by a second wash with 250 µl 70% ethanol and centrifugation for 3 minutes at 11,000×g at RT. The small RNA enriched sample was eluted from the spin column with 40 µl water and centrifugation for 1 minute at 11,000×g at RT.

RNA tailing and reverse transcription into cDNA was performed in one simultaneous reaction using 50 ng to 400 ng of small RNA sample. The typical 10 µl reaction mixture consisted of 0.8 µM reverse transcription DNA primer (DNA Sequence #1), 10 mM tris-HCl, pH 8.0, 75 mM KCl, 10 mM DTT, 500 µM ATP, 2.5 mM each dGTP, dATP, dTTP & dCTP, 1 U *E. coli* Poly(A) Polymerase (New England Biolabs), 160 U M-MLV reverse transcriptase (Promega) and 70 mM MgCl$_2$. However, depending on the experiment other MgCl$_2$ concentrations may have been used, specifically 3 mM, 20 mM and 50 mM. After mixing the components and briefly centrifuging, the reaction was incubated at 37° C. for 30 minutes followed by 95° C. for 5 minutes. The resulting sample cDNA was then placed on ice and diluted with 90 µl nuclease-free water (10 fold) so that 1 µl (1/100) was used as the template for each individual 25 µl PCR reaction.

The amount of specific miRNA sequences present in the samples was quantified by SYBR® Green real-time PCR. Individual samples were assayed by combining 12.5 µl 2×SYBR® Green PCR Master Mix (ABI) with 1 µl cDNA sample, 1 µl PCR primer mixture containing 10 µM each, specific forward (DNA Sequences #2 through #6) and universal reverse primer (DNA Sequence #7) and 9.5 µl nuclease-free water. Real-time PCR thermal cycling and detection was performed on either an ABI 7500, ABI7900 or Stratagene Mx3005P instruments. Thermal cycling conditions were programmed to be 10 minutes at 95° C. then 40 cycles of 15 seconds at 95° C., 30 seconds at 60° C. and 60 seconds at 72° C. and concluding with the instrument specific thermal dissociation sub-program.

Using the instrument's software and a consistent selection of measurement variables, Ct values were determined. Once control reaction results were assessed for a consistent quality criteria, relative miRNA expression measurements could be obtained by the ΔΔCt calculation method (Livak 2001) using the average Ct of four constitutively expressed small RNA assays to normalize the data within each sample.

In addition, assays were evaluated for specificity of the PCR by analyzing the first derivative of the thermal dissociation profiles from the final reaction products. This method of analysis allowed the determination of the extent to which RNAs other than the intended target were tailed and then amplified in the PCR (FIG. 1). The various products exhibit melting peaks along the temperature axis, and the apex of each peak and its symmetry are indicative of the purity of the resulting product. The melting profiles of the products generated from the reaction in which tailing and reverse transcription was carried out at magnesium ion concentrations of 50 mM and 70 mM reflected the greater specificity of tailing than those carried out at lower magnesium concentrations (FIG. 2) and indicated that less non-specific tailing and subsequent PCR amplification resulted when these conditions of elevated magnesium were used.

hsa-miR-658 Amplification

Figure 2A:
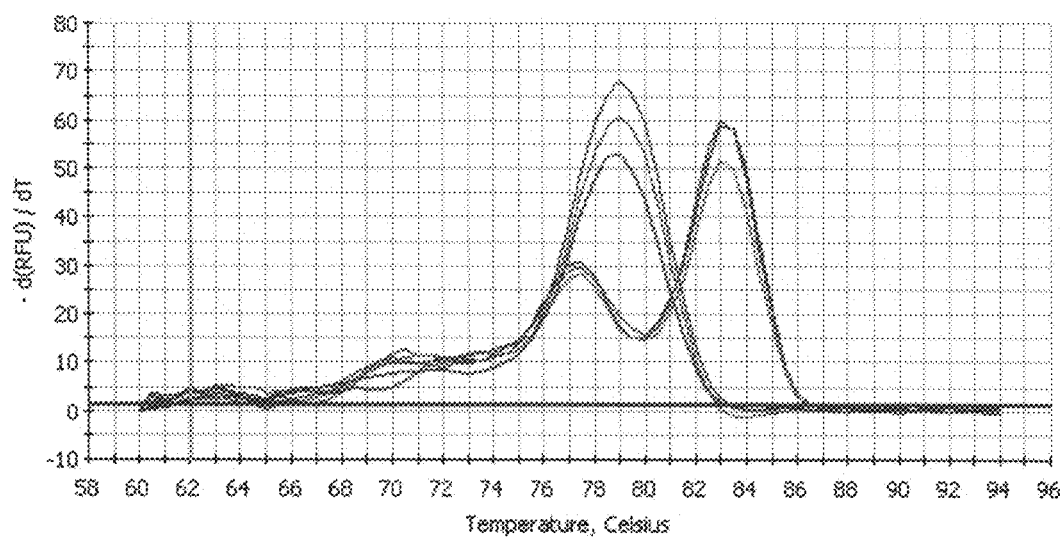
FIGS. 2A-2D show that, when a high input of hsa-mir-658 RNA (120,400 copies) is added (FIGS. 2A and 2B) against a background of small RNA from 293 cells, low Mg++ concentration (3 mM) in the tailing and reverse transcription reactions results in substantial amplification of non-specific targets and at this hsa-mir-658 RNA input higher Mg++ concentrations (20 mM, 50 mM and 70 mM) yield only amplification of the desired target (peak at Tm 79° C.). At 100 fold lower input hsa-mir-658 RNA (1204 copies) (FIGS. 2C and 2D) only concentrations of 50 mM and 70 mM Mg++ in the tailing and reverse transcription reactions resulted in amplification of only the desired target, though use of 20 mM Mg++ resulted in less amplification of non-specific RNA than use of 3 mM Mg++.
Figure 2B:
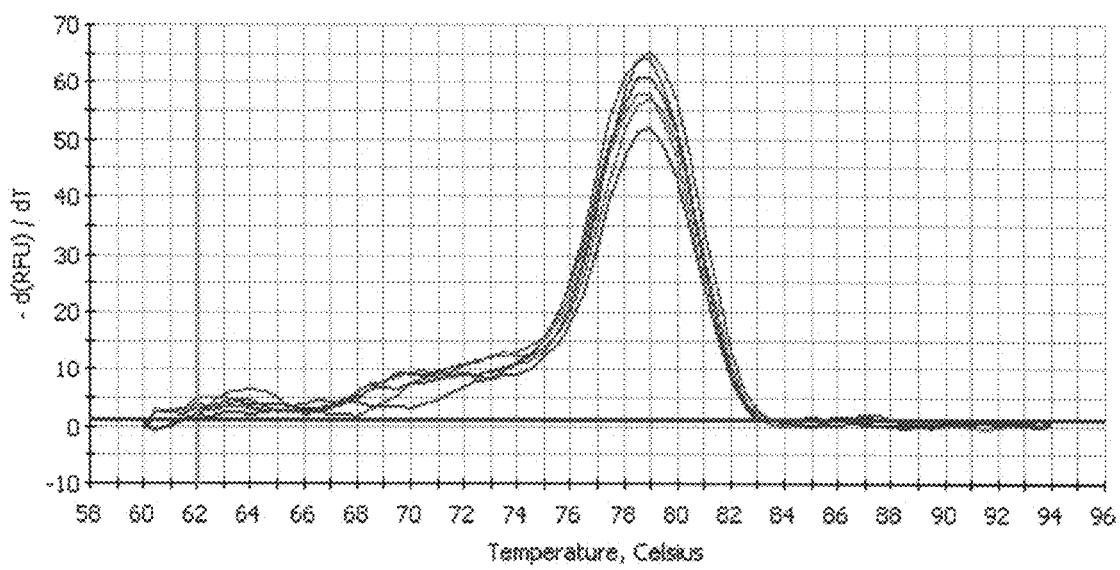
Figure 2C:
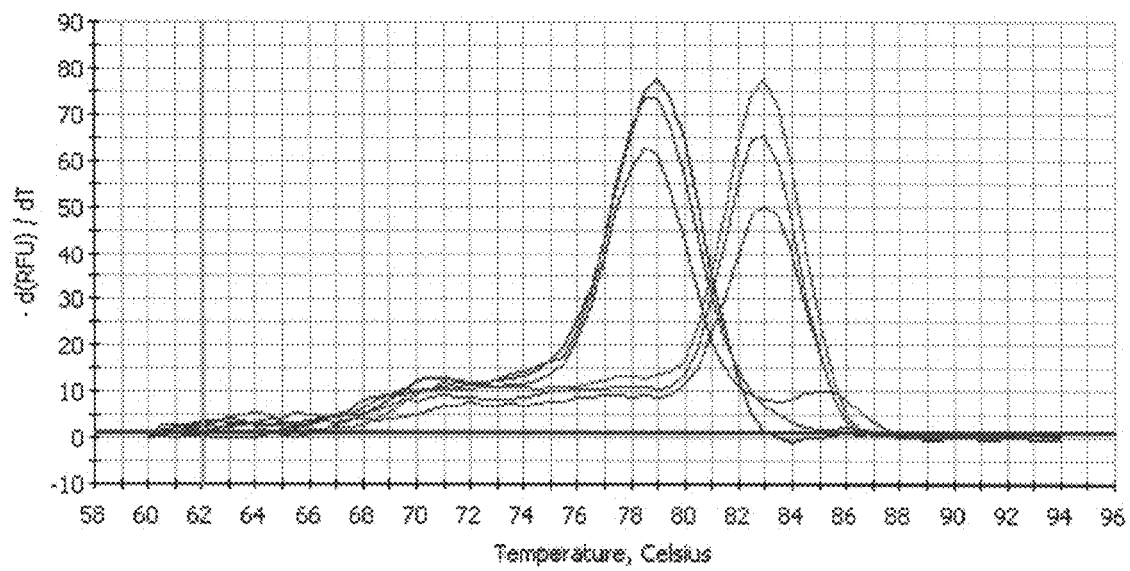
Figure 2D:
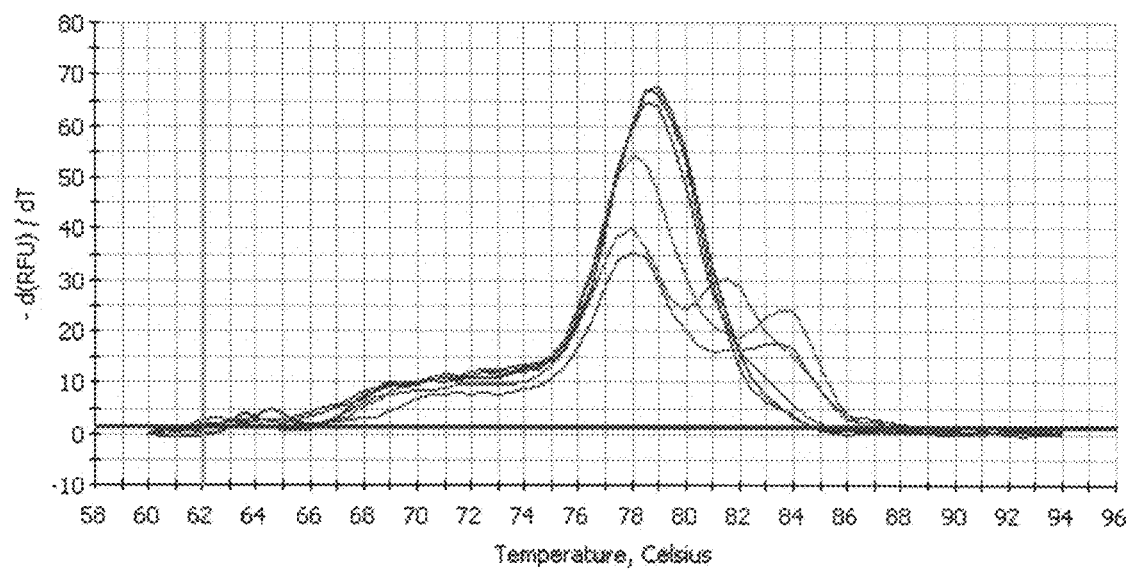
Figure 3:
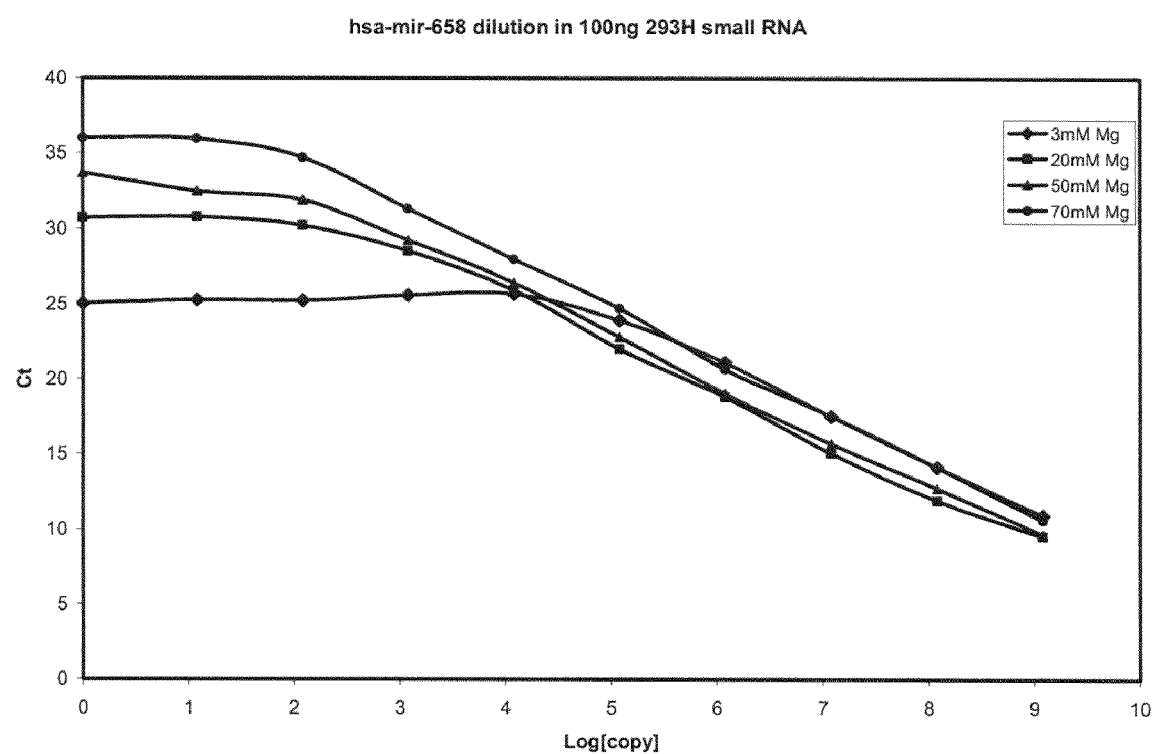
FIG. 3 shows the real-time PCR (qPCR) results (Ct values) for a miR-658 specific assay from 10-fold serial dilutions of the hsa-mir-658 synthetic RNA oligonucleotide into 100 ng small RNAs from 293H cells in which four different concentrations of Mg++ ions (3, 20, 50 and 70 mM) were used during the poly(A) tailing and reverse transcriptase reactions. In order to simulate a uniform complex nucleic acid background in the miRNA RT-qPCR process, a constant amount (10 ng/µl) of 293H cell small RNA was included in every sample and therefore contributes a uniform background as seen in the low copy number data points. This background signal decreases with increasing Mg++ levels so that it is 1663-fold lower when 70 mM Mg++ is used in the enzymatic reactions than when 3 mM Mg++ is used. The linearity of the signal with decreasing target input continues to lower target inputs when the higher Mg++ concentrations are used thereby providing a more sensitive assay and one which can be quantitative at lower target concentrations.
Figure 4A:
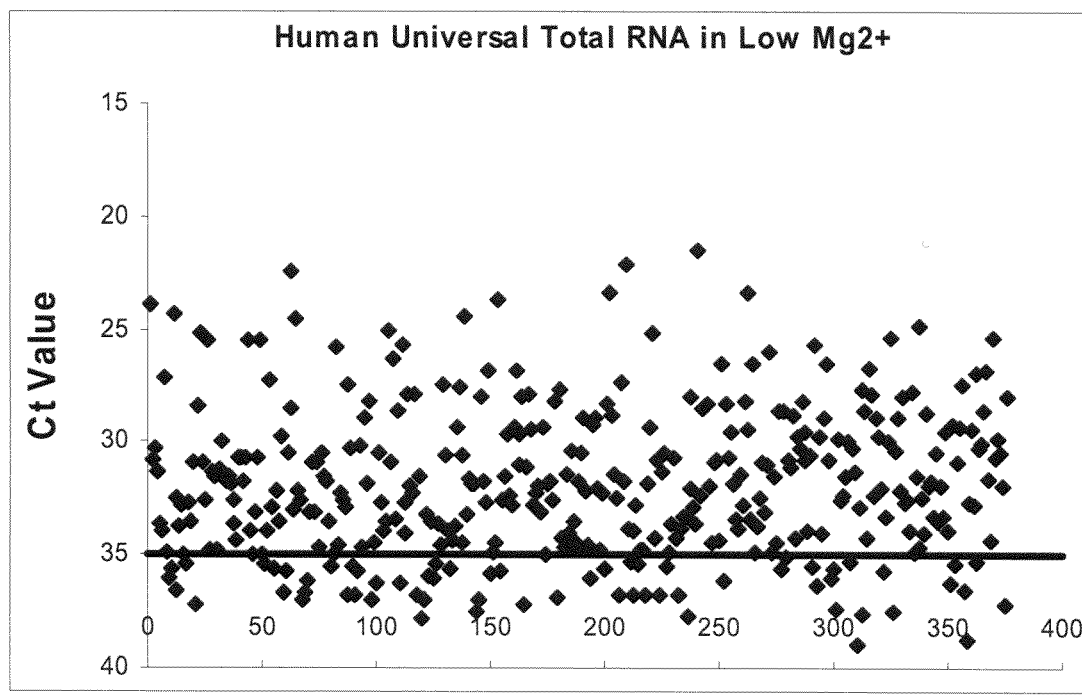
Figure 4B:
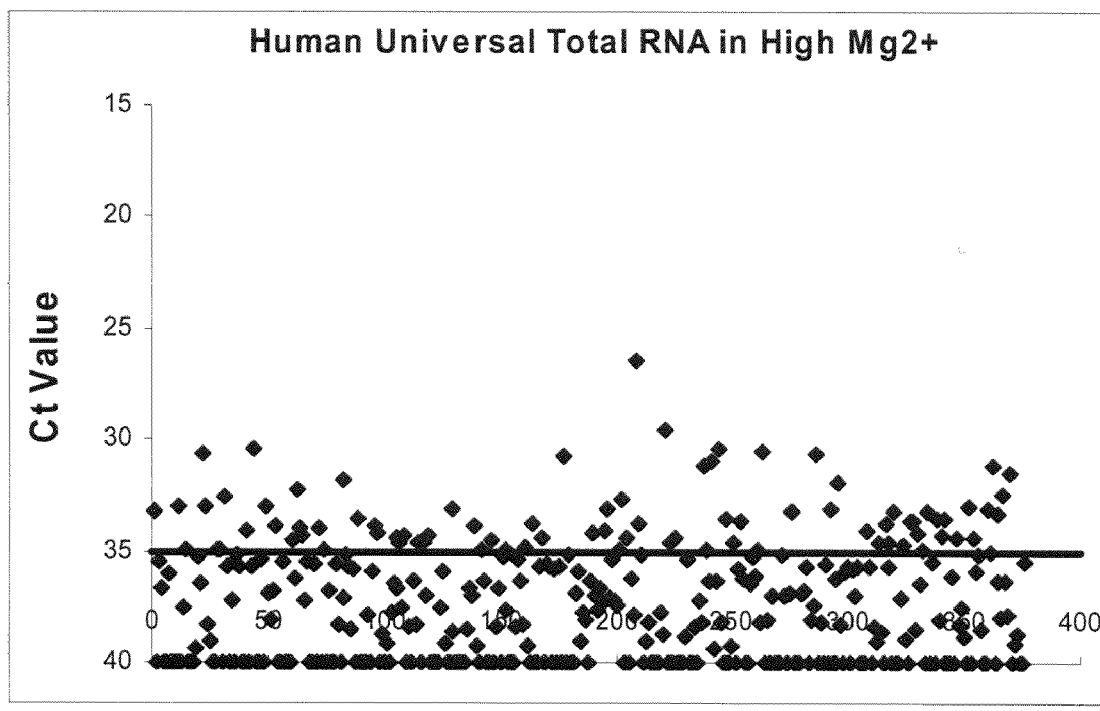

For the experiments shown in FIG. 2A, 120,400 copies of synthetic has-miR-658 were spiked into a sample containing 100 ng 293H small RNA. Polyadenylation and reverse transcriptase reactions were run in triplicate in the presence of 3 and 70 mM MgCl$_2$. FIG. 2B shows the results for reactions run in the presence of 20 and 50 mM MgCl$_2$. The reaction products were analyzed by PCR. An oligonucleotide of the sequence set forth in SEQ ID NO:1 was used as the reverse transcription primer for poly(A) tailed RNA, the miRNA specific primer had the sequence set forth in SEQ ID NO:6 and was used with the reverse universal primer of SEQ ID NO:7.

Figure 5A:
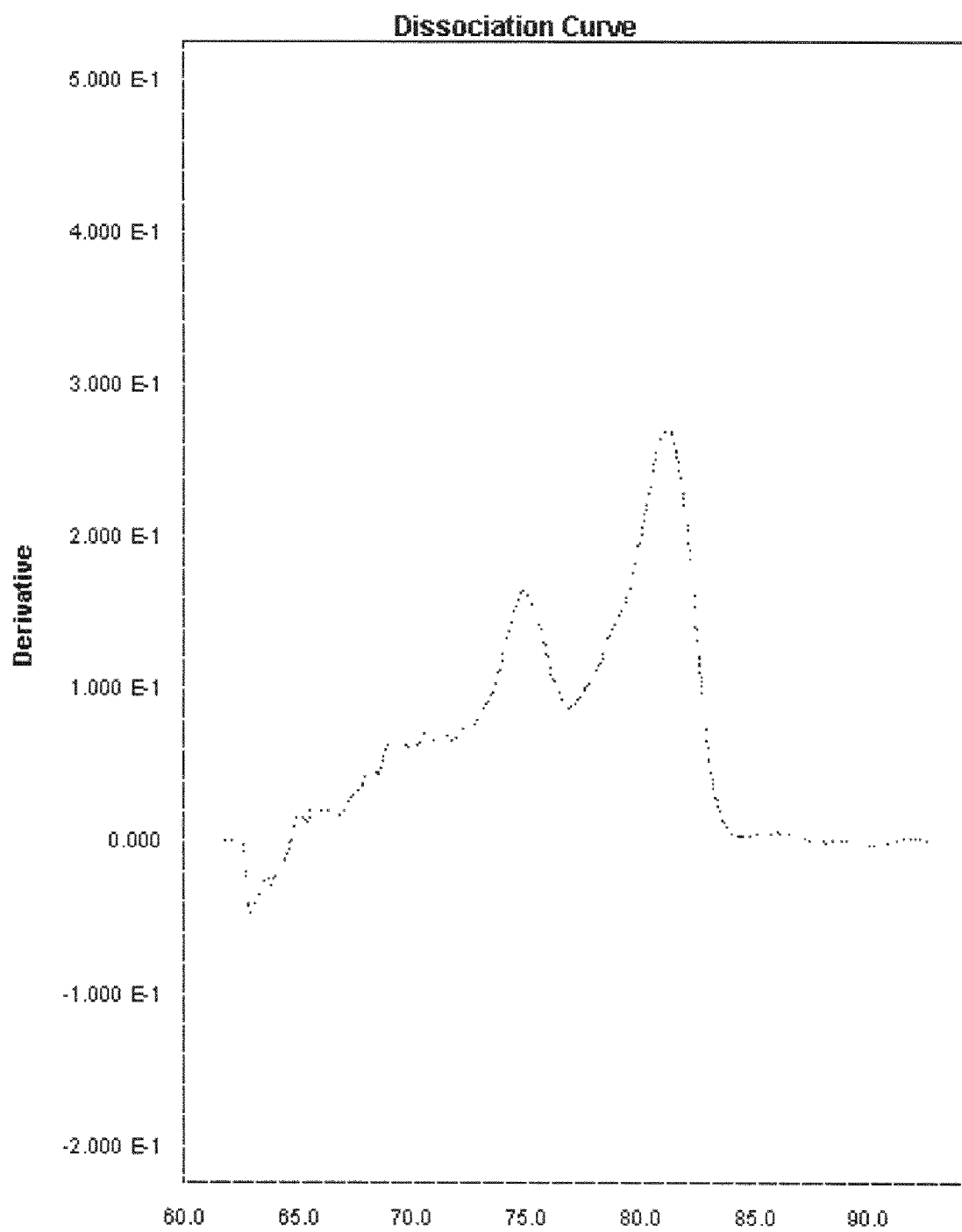
FIG. 5 shows the thermal dissociation curves for four additional miRNA RT-qPCR assays for hsa-miR-10a (FIGS. 5A and 5B), hsa-miR-346 (FIGS. 5C and 5D), hsa-miR-504 (FIGS. 5E and 5F), and hsa-miR-555 (FIGS. 5G and 5H), where "Bad Assay" results are obtained under 3 mM Mg conditions (FIGS. 5A, 5C, 5E and 5G) and good results are obtained using 70 mM Mg (FIGS. 5B, 5D, 5F and 5H).
Figure 5B:
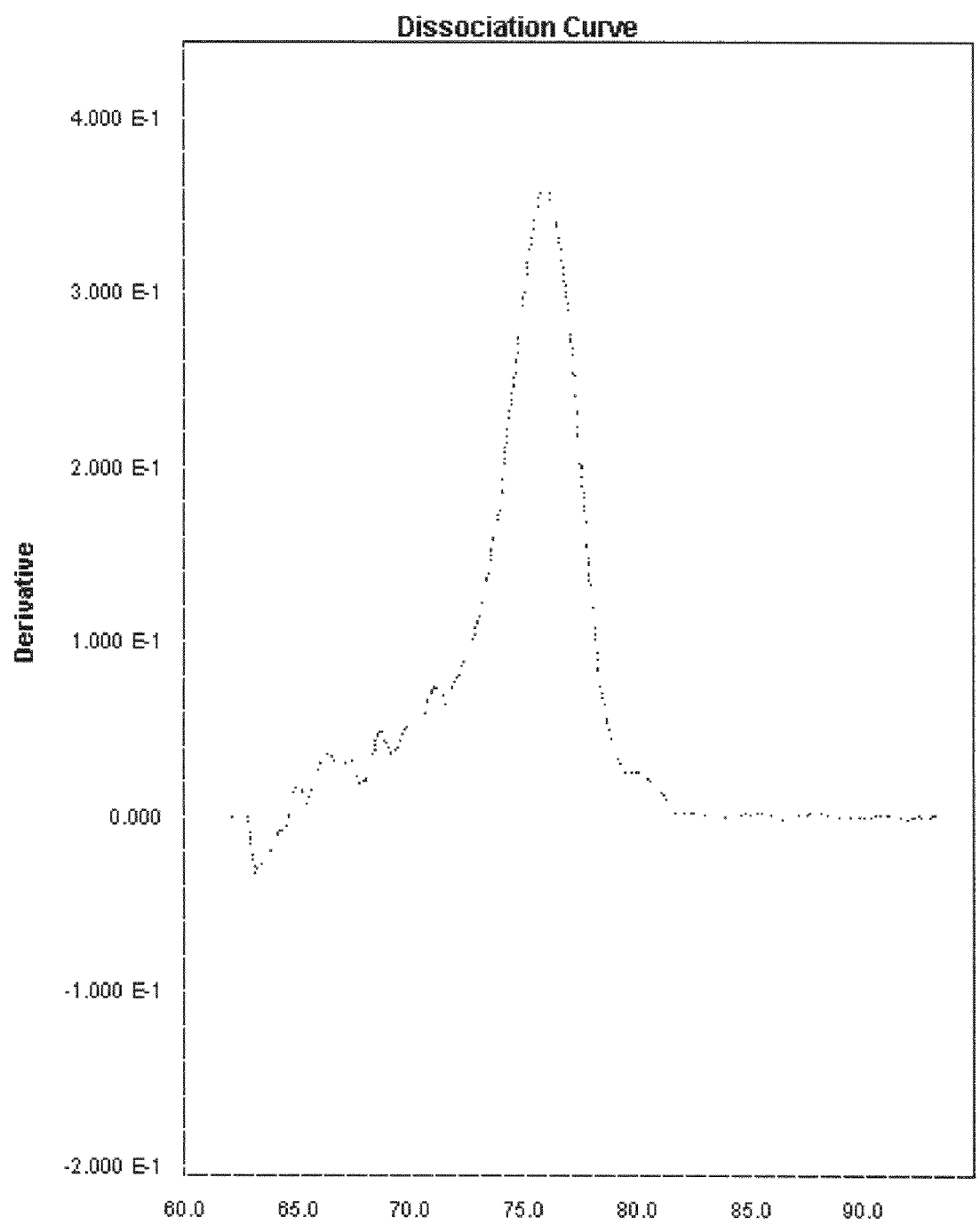

For amplifications of hsa-miR-10a, shown in FIGS. 5A and 5B, the experiments were carried out as described above with 3 or 70 mM Mg cation, but using the oligonucleotide of SEQ ID NO:3 as forward primer.

Figure 5C:
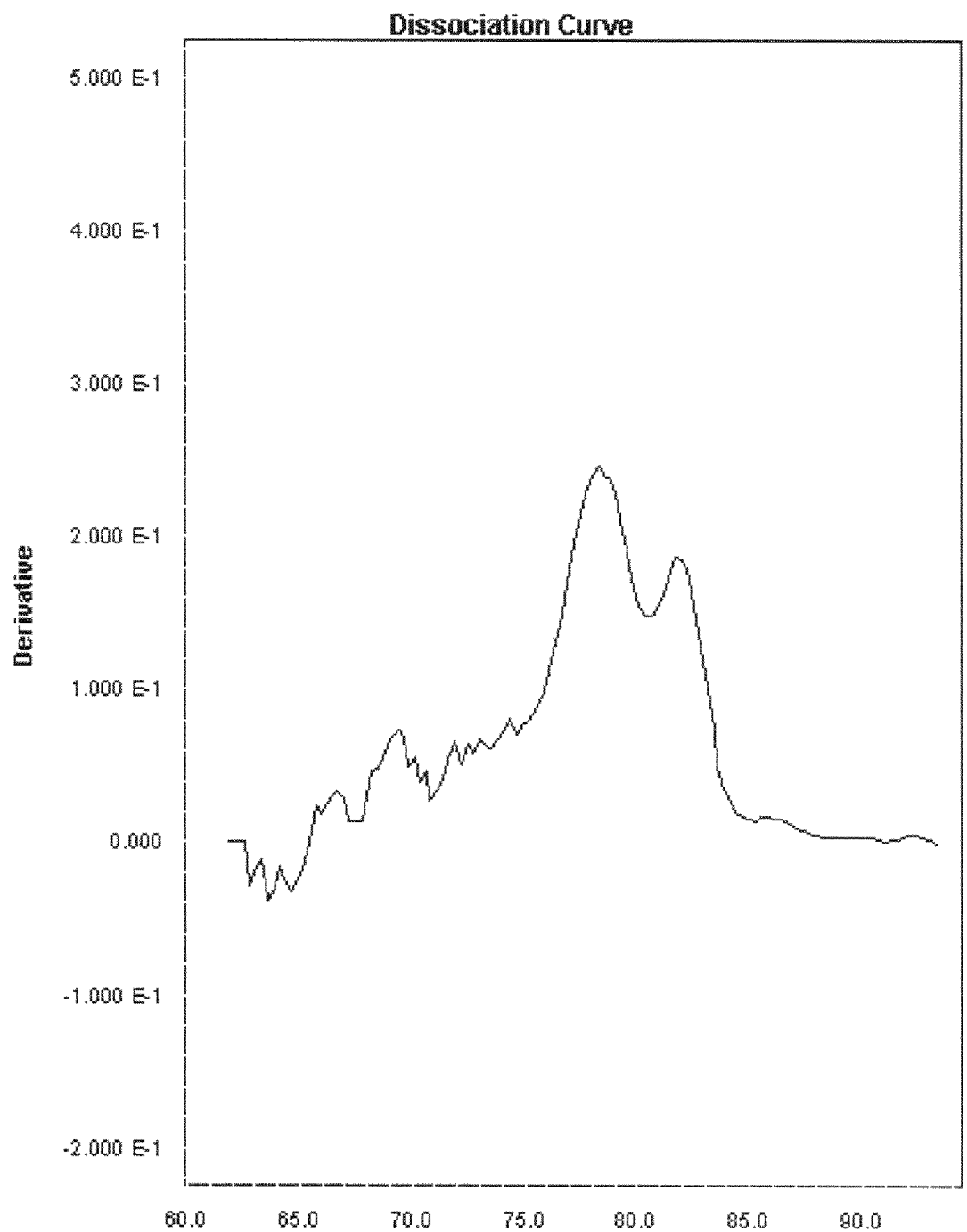
Figure 5D:
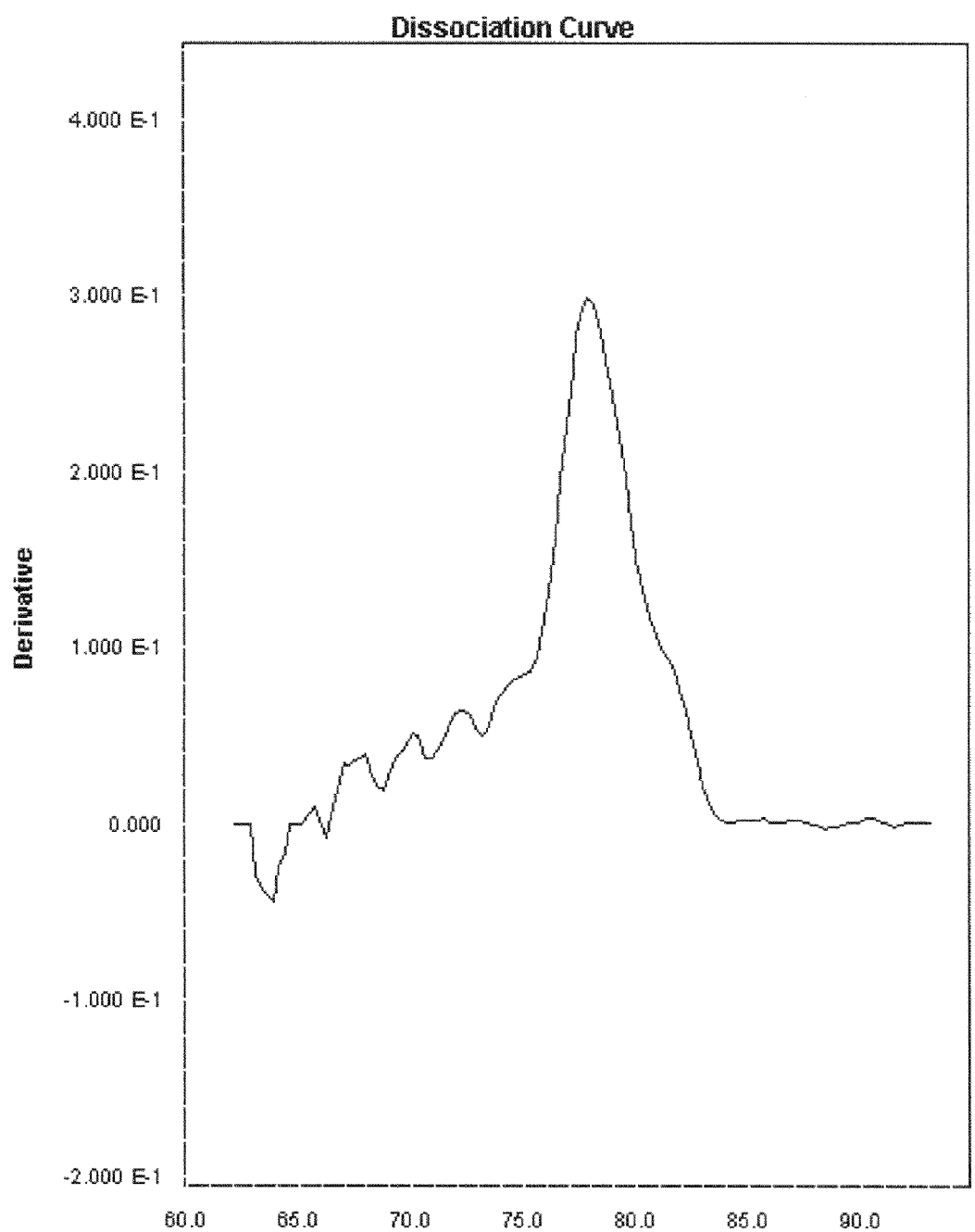

For amplifications of hsa-miR-346, shown in FIGS. 5C and 5D, the experiments were carried out as described above with 3 or 70 mM Mg cation, but using the oligonucleotide of SEQ ID NO:2 as forward primer.

Figure 5E:
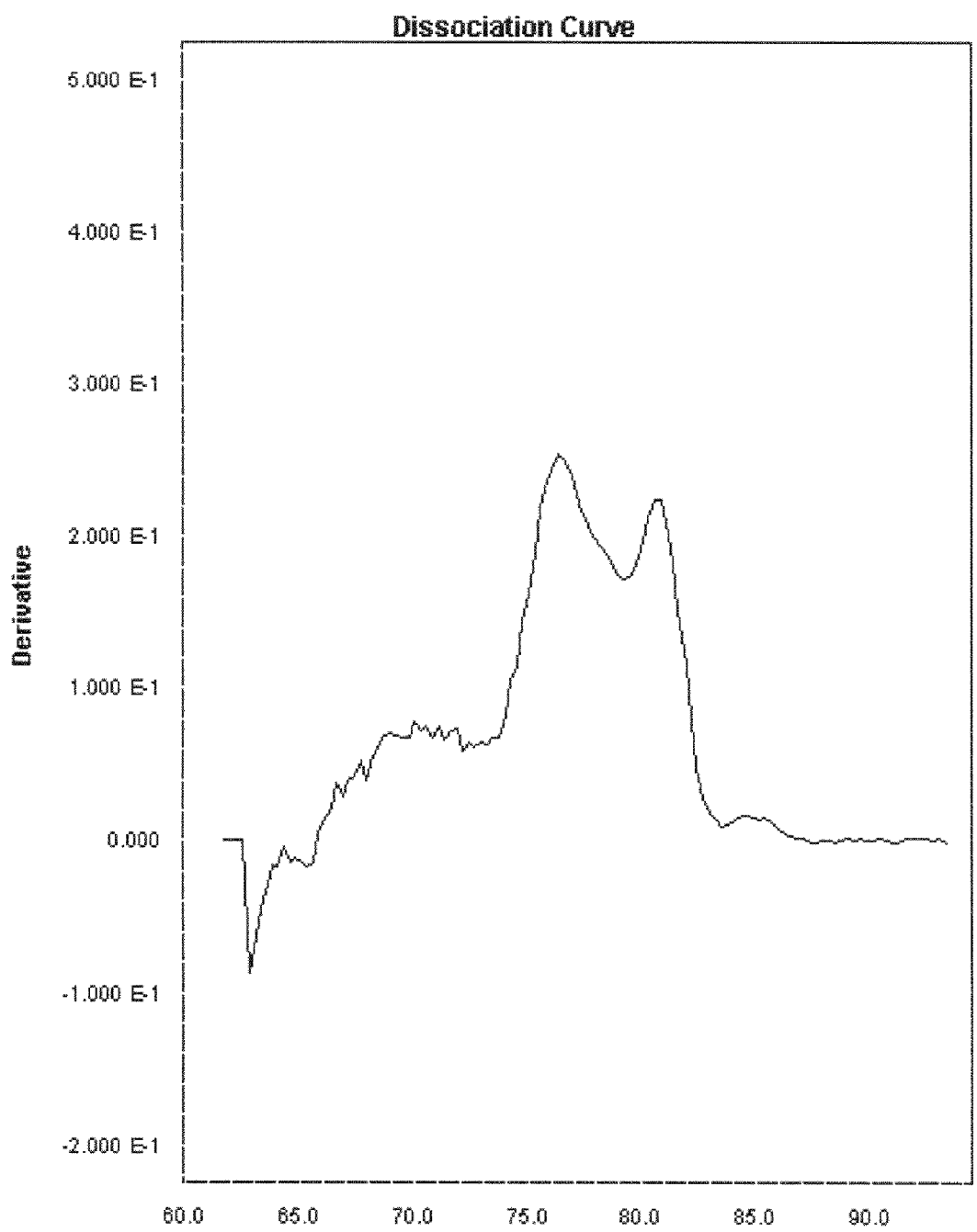
Figure 5F:
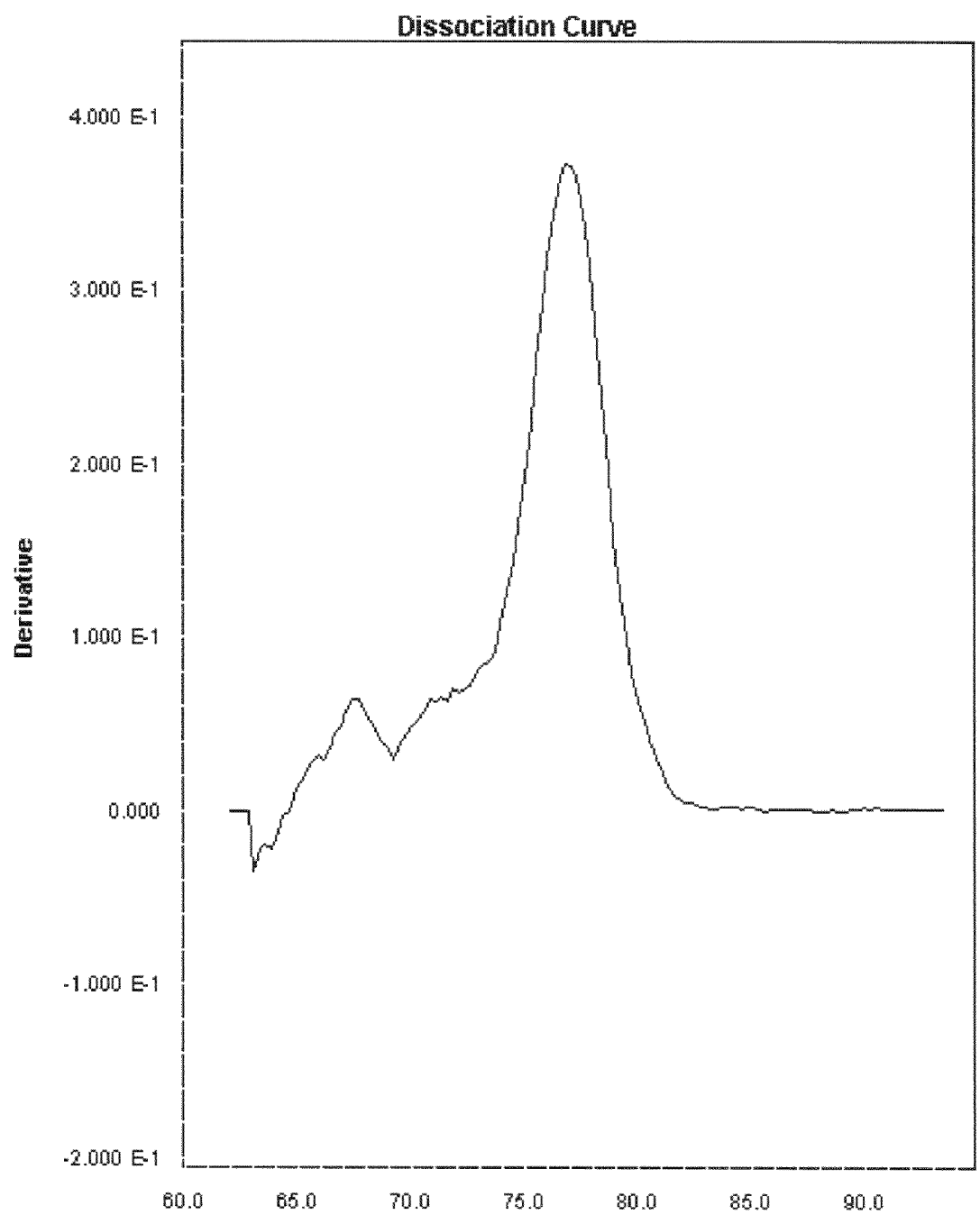

For amplifications of hsa-miR-504, shown in FIGS. 5E and 5F, the experiments were carried out as described above with 3 or 70 mM Mg cation, but using the oligonucleotide of SEQ ID NO:4 as forward primer.

Figure 5G:
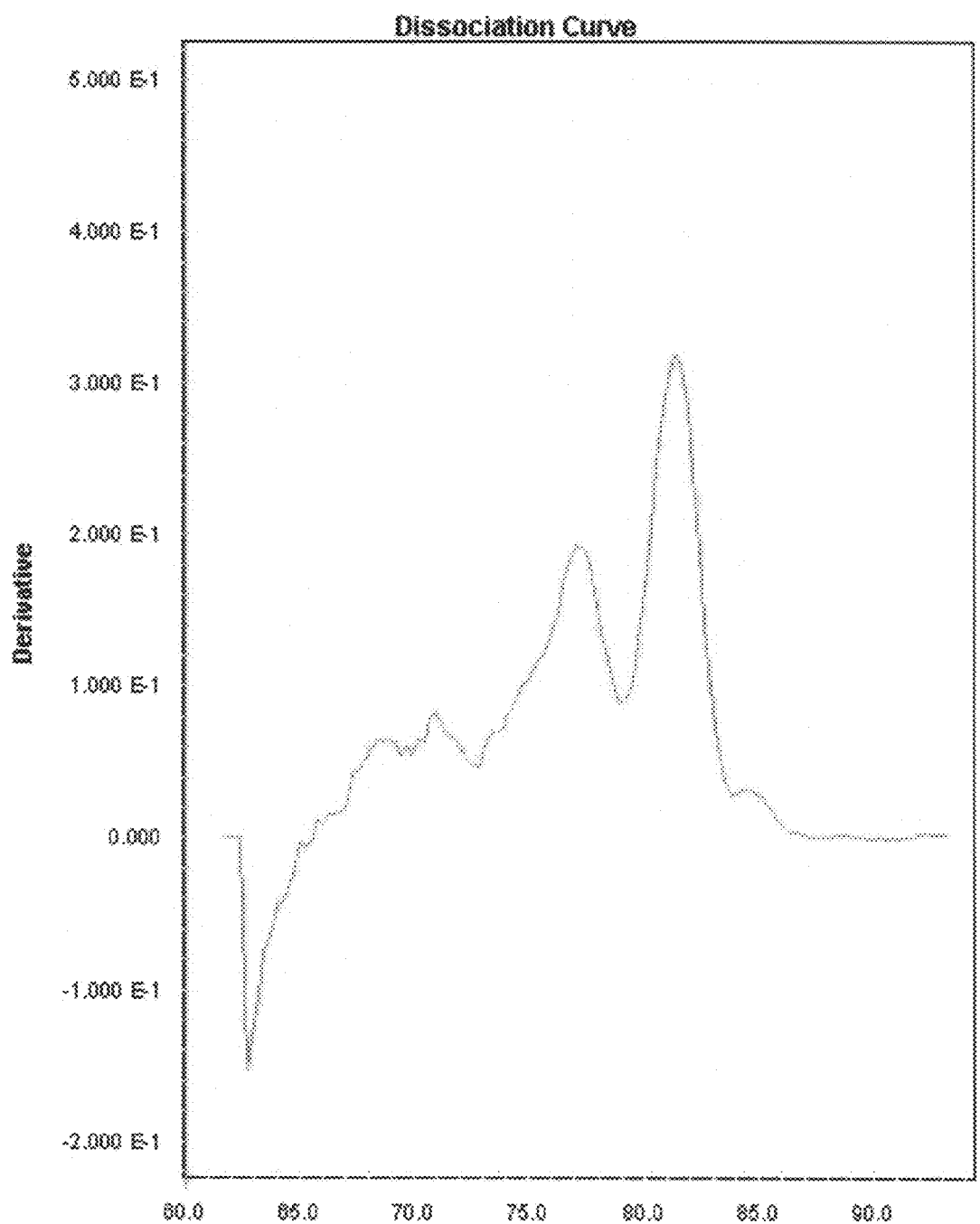
Figure 5H:
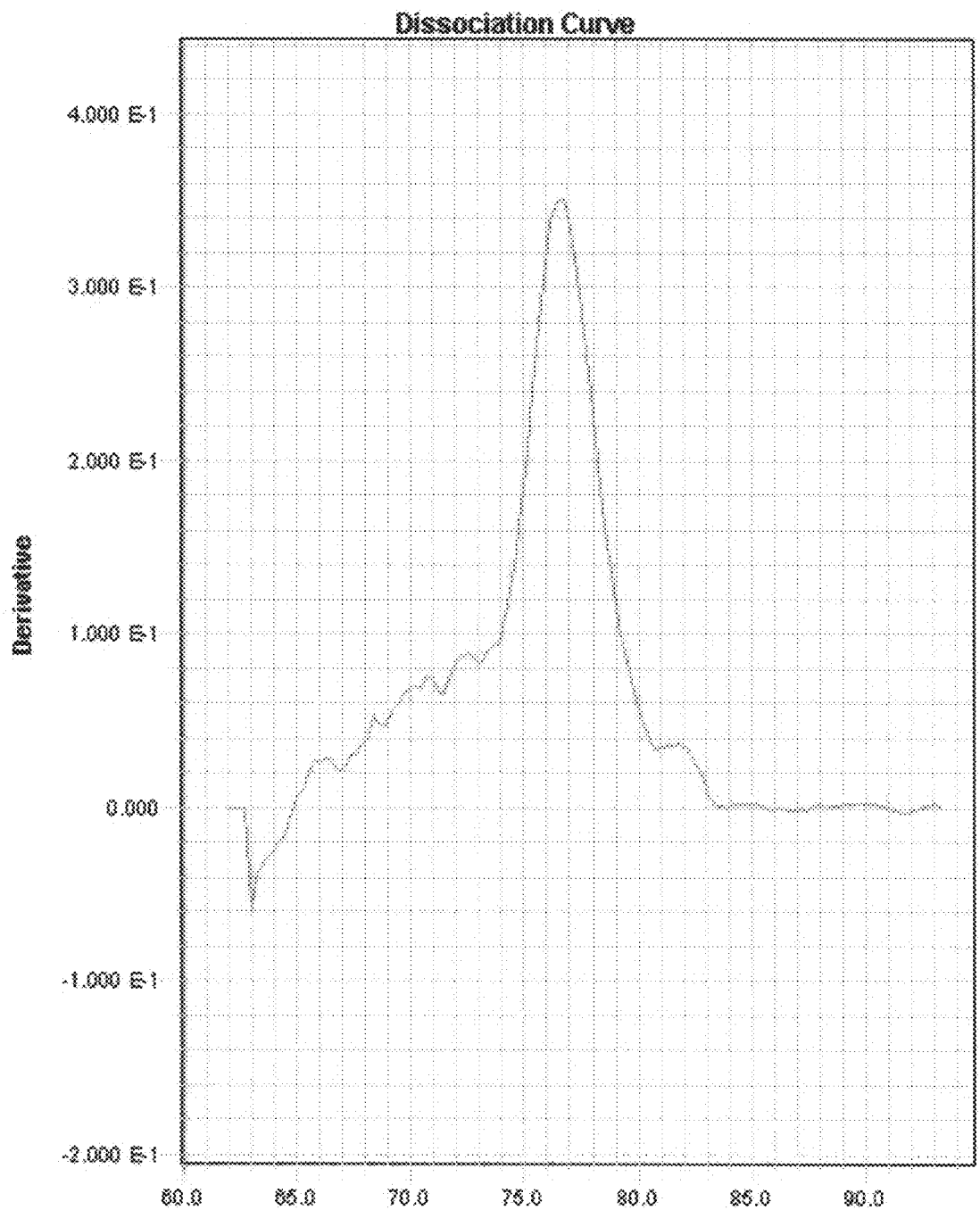

For amplifications of hsa-miR-555, shown in FIGS. 5G and 5H, the experiments were carried out as described above with 3 or 70 mM Mg cation, but using the oligonucleotide of SEQ ID NO:5 as forward primer.

All sequences are written in 5' to 3' orientation. All miRNA accession numbers and sequences used for primer design are from the public database, miRBase, v10.0 (internet address, microrna.sanger.ac.uk/sequences/).

1) Reverse transcription (RT) primer for poly(A) tailed RNA:
SEQ ID NO:1,
GTGCAGGGTCCGAGGTTCACTATAGGTTTTTTTTTTTTTTTTTTTTTT VN
where V is G, A or C and N is G, A, T or C 2) Forward PCR primer for hsa-miR-346 (MIMAT0000773): SEQ ID NO:2,
TGTCTGCCCGCATGCCTGCCTCT 3) Forward PCR primer for hsa-miR-10a (MIMAT0000253): SEQ ID NO:3,
TACCCTGTAGATCTGAATTTGTG 4) Forward PCR primer for hsa-miR-504 (MIMAT0002875): SEQ ID NO:4,
ACCCTGGTCTGCACTCTATCAA 5) Forward PCR primer for hsa-miR-555 (MIMAT0003219): SEQ ID NO:5,
GGTAAGCTGAACCTCTGATAA 6) Forward PCR primer for hsa-miR-658 (MIMAT0003336): SEQ ID NO:6,
GGCGGAGGGAAGTAGGTCCGTTGGT 7) Universal reverse PCR primer for cDNAs generated from the RT primer above:
SEQ ID NO:7, GTGCAGGGTCCGAGGT

---

We claim:

1. A method for preparing a cDNA copy of a small RNA molecule, comprising:
   (a) providing a small RNA from a biological sample, wherein said RNA is from 18 to 28 nucleotides in length;
   (b) incubating the small RNA with an enzyme capable of catalyzing the addition of nucleotides at the 3' end of the small RNA in the presence of a single ribonucleotide triphosphate selected from the group consisting of ATP, GTP, UTP, and CTP and at a final concentration of divalent magnesium cation between 50 millimolar and 70 millimolar in a reaction to add nucleotides to the small RNA to generate a tailed small RNA;
   c) annealing a DNA primer to the tailed small RNA whereby the DNA template extends from the 3' end of the tailed small RNA, thereby providing a single stranded region of DNA that may be used to direct polymerization of deoxyribonucleotide triphosphates; and
   (d) incubating the annealed tailed small RNA and DNA primer in the presence of reverse transcriptase; and deoxyribonucleotide triphosphates and at a final concentration of divalent magnesium cation between 50 millimolar and 70 millimolar under conditions allowing reverse transcription into cDNA and amplification of the annealed tailed small RNA to produce an amplification product.

2. The method of claim 1, wherein the enzyme used in step (b) is *Escherichia coli* Poly(A) polymerase.

3. The method of claim 1, wherein polymerization in step (c) is catalyzed by is MMLV reverse transcriptase.

4. The method of claim 1, wherein the steps (b), (c) and (d) are performed concurrently in a single reaction mixture.

5. The method of claim 1, further comprising the step of quantifying the amplification product of step (d).

6. The method of claim 1, further comprising the step of detecting the amplification product of step (d).

7. The method of claim 4, further comprising the step of quantifying the amplification product of step (d).

8. The method of claim 4, further comprising the step of detecting the amplification product of step (d).

* * * * *

UNITED STATES PATENT AND TRADEMARK OFFICE
CERTIFICATE OF CORRECTION

| | | |
|---|---|---|
| PATENT NO. | : 8,399,221 B2 | Page 1 of 1 |
| APPLICATION NO. | : 12/291010 | |
| DATED | : March 19, 2013 | |
| INVENTOR(S) | : Daniel Y. Kim et al. | |

It is certified that error appears in the above-identified patent and that said Letters Patent is hereby corrected as shown below:

In the Claims:

Column 13, Line 58:

"primer in the presence of reverse transcriptase; and" should read, --primer in the presence of reverse transcriptase and--.

Signed and Sealed this
Thirtieth Day of July, 2013

Teresa Stanek Rea
*Acting Director of the United States Patent and Trademark Office*